(12) United States Patent
Pinchasik

(10) Patent No.: US 6,796,999 B2
(45) Date of Patent: Sep. 28, 2004

(54) SELF ARTICULATING STENT

(75) Inventor: Gregory Pinchasik, Herzlia (IL)

(73) Assignee: Medinol Ltd., Tel Aviv (IL)

( * ) Notice: Subject to any disclaimer, the term of this patent is extended or adjusted under 35 U.S.C. 154(b) by 0 days.

(21) Appl. No.: 10/232,618

(22) Filed: Sep. 3, 2002

(65) Prior Publication Data

US 2003/0045926 A1 Mar. 6, 2003

Related U.S. Application Data

(60) Provisional application No. 60/317,185, filed on Sep. 6, 2001.

(51) Int. Cl.$^7$ .................................................. A61F 2/06
(52) U.S. Cl. ...................................................... 623/1.16
(58) Field of Search ............................... 623/1.15, 1.16, 623/1.17, 1.18, 1.19, 1.2, 1.21, 1.22, 23.7

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,856,516 A | 8/1989 | Hillstead |
| 4,886,062 A | 12/1989 | Wiktor |
| 4,969,458 A | 11/1990 | Wiktor |
| 5,019,090 A | 5/1991 | Pinchuk |
| 5,102,417 A | 4/1992 | Palmaz |
| 5,104,404 A | 4/1992 | Wolff |
| 5,116,365 A | 5/1992 | Hillstead |
| 5,135,536 A | 8/1992 | Hillstead |
| 5,161,547 A | 11/1992 | Tower |
| 5,282,824 A | 2/1994 | Gianturco |
| 5,383,892 A | 1/1995 | Cardon et al. |
| 5,449,373 A | 9/1995 | Pinchasik et al. |
| 5,591,197 A | 1/1997 | Orth et al. |
| 5,591,223 A | 1/1997 | Lock et al. |
| 5,593,442 A | 1/1997 | Klein |
| 5,723,003 A | 3/1998 | Winston et al. |
| 5,733,303 A | 3/1998 | Israel et al. |
| 5,735,893 A | * 4/1998 | Lau et al. .................. 623/1.16 |
| 5,755,781 A | 5/1998 | Jayaraman |
| 5,807,404 A | 9/1998 | Richter |
| 5,836,966 A | 11/1998 | St. Germain |
| 5,964,770 A | 10/1999 | Flomenblit et al. |
| 6,258,117 B1 | * 7/2001 | Camrud et al. ............. 623/1.16 |
| 6,270,524 B1 | 8/2001 | Kim |
| 6,485,510 B1 | 11/2002 | Camrud et al. |
| 2002/0055770 A1 | * 5/2002 | Doran et al. ................ 623/1.15 |

FOREIGN PATENT DOCUMENTS

| | | |
|---|---|---|
| EP | 0 806 190 | 11/1997 |
| EP | 1005843 A2 | 6/2000 |
| EP | 1 110 515 | 6/2001 |
| EP | 1 129 673 | 9/2001 |
| GB | 2360456 A | 9/2001 |
| WO | WO 97/37617 | 10/1997 |
| WO | WO 99/17680 | 4/1999 |
| WO | WO 00/30563 | 6/2000 |
| WO | WO 01/08600 | 2/2001 |

* cited by examiner

Primary Examiner—Corrine McDermott
Assistant Examiner—Thomas J Sweet
(74) Attorney, Agent, or Firm—Kenyon & Kenyon

(57) ABSTRACT

A stent is made up of a plurality of adjacent stern segments, spaced from one another. Between each two adjacent stent segments is a detachment zone that includes two articulation planes. In each articulation plane there are two connecting members, with the members in one articulation plane spaced from those in the other articulation plane about the circumference of the stent by from about 60 to 140 degrees from each other. Within each articulation plane, the two members are spaced between about 140 and 220 degrees from each other.

15 Claims, 5 Drawing Sheets

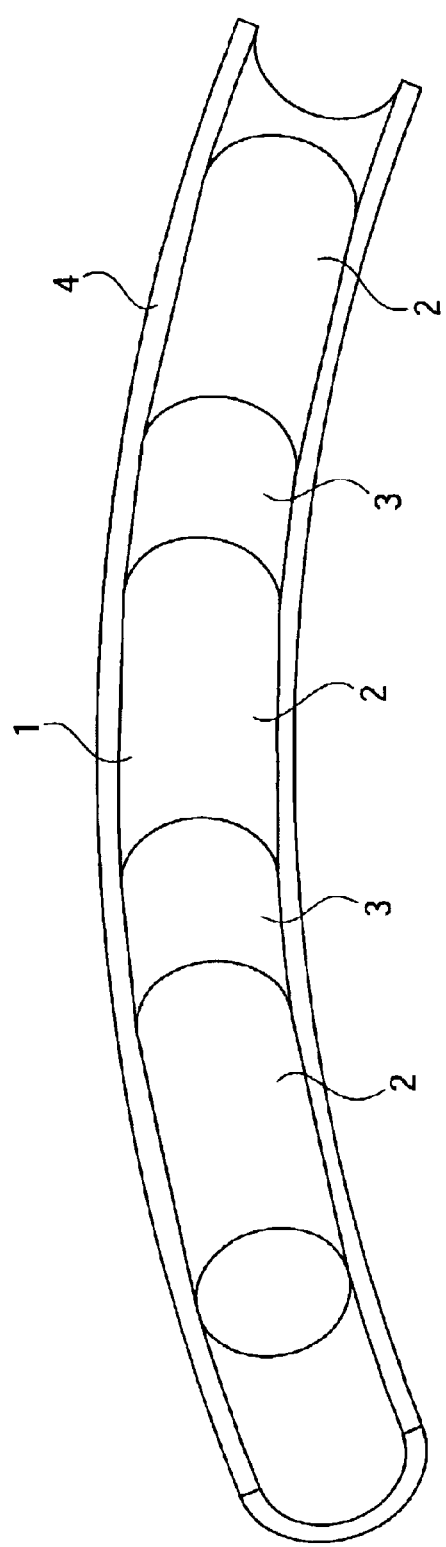
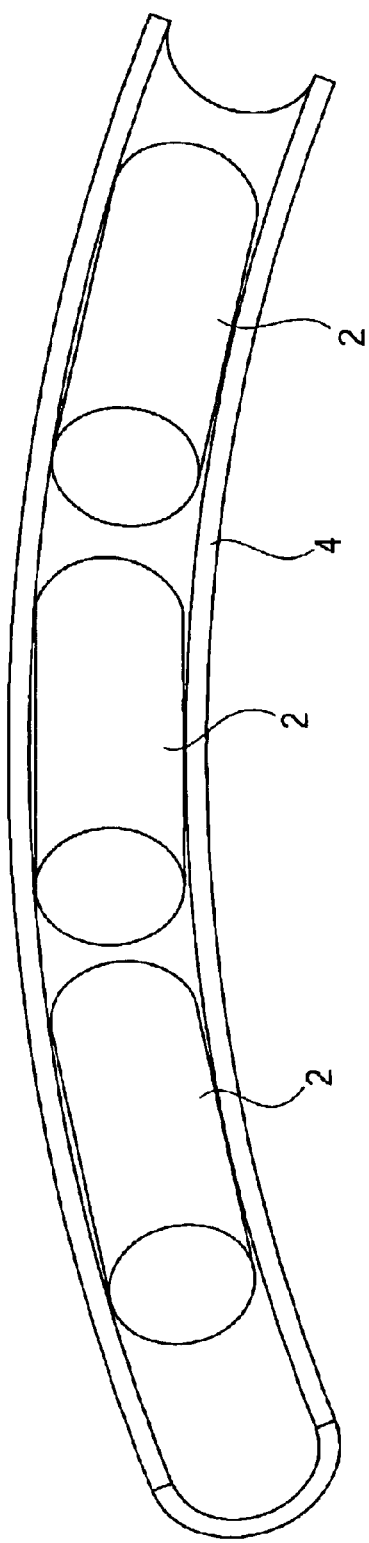
Fig. 1
Fig. 2

SELF ARTICULATING STENT

CROSS REFERENCE TO RELATED CASES

Applicant claims the benefit of U.S. Provisional Ser. No. 60/317,185 filed Sep. 6, 2001

BACKGROUND OF THE INVENTION

This invention relates generally to stents, which are endoprostheses implanted into vessels within the body, such as a blood vessels, to support and hold open the vessels, or to secure and support other endoprostheses in vessels in general and more particularly to a self articulating stent.

Various stents are known in the art. Typically stents are generally tubular in shape, and are expandable from a relatively small, unexpanded diameter to a larger, expanded diameter. For implantation, the stent is typically mounted on the end of a catheter, with the stent being held on the catheter at its relatively small, unexpanded diameter. The catheter directs the unexpanded stent directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

Some examples of patents relating to stents include U.S. Pat. No. 4,733,665 to Palmaz; U.S. Pat. Nos. 4,800,882 and 5,282,824 to Gianturco; U.S. Pat. Nos. 4,856,516 and 5,116,365 to Hillstead; U.S. Pat. Nos. 4,886,062 and 4,969,458 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373 to Pinchasik et al.; and U.S. Pat. No. 5,733,303 to Israel et al.

One object of prior stent designs has been to insure that the stent has sufficient radial strength when it is expanded so that it can sufficiently support the lumen. Stents with high radial strength, however, tend also to have a higher longitudinal rigidity than the vessel in which it is implanted. When the stent has a higher longitudinal rigidity than the vessel in which it is implanted, increased trauma to the vessel may occur at the ends of the stent, due to stress concentrations on account of the mismatch in compliance between the stented and un-stented sections of the vessel.

Thus, there is a need to provide a stent that more closely matches the compliance of the vessel, in which it is implanted, with relatively little or no sacrifice in radial strength, even when the stent is made very long.

SUMMARY OF THE INVENTION

In accordance with embodiments of the present invention, improved compliance with relatively little or no sacrifice in radial strength, even when the stent is made very long, is accomplished by dividing the stent into segments separated by self articulation areas, each comprising two articulation planes in which there are two thin members, with the members in one articulation plane spaced from those in the other articulation plane about the circumference of the stent by an amount as close to 90 degrees as possible for a particular configuration.

BRIEF DESCRIPTION OF THE DRAWINGS

FIG. 1 is a schematic perspective view of a stent, generally in the form of a cylinder, having designated articulation zones between stent segments, disposed in a curved vessel.

FIG. 2 is a schematic perspective view of the stent of FIG. 1 after detachment, in which the stent has separated into a series of shorter stent segments.

DETAILED DESCRIPTION

Figure 3:
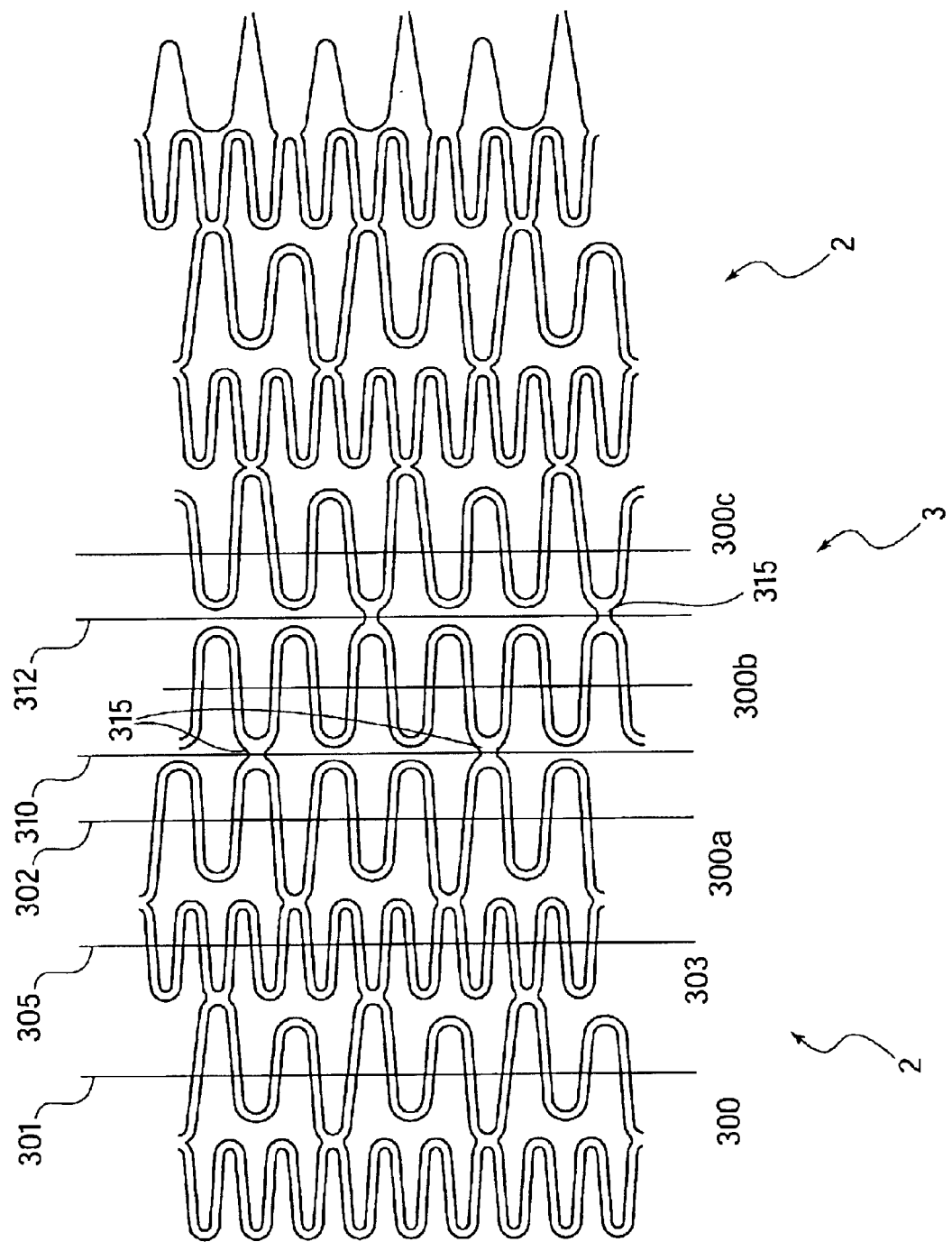
FIG. 3 shows a flat layout of a stent pattern in which the designated detachment zone includes two articulation planes, each with two thin members with the members in one articulation plane spaced from those in the other articulation plane about the circumference of the stent by approximately 90 degrees.

FIG. 1 is a schematic perspective view of a stent 1, generally in the form of a cylinder disposed in a curved vessel 4. The stent 1 comprises a series of stent segments 2 separated by designated detachment zones 3. In one embodiment, the designated detachment zones 3 each comprise two articulation planes in each of which two easily breakable areas, e.g., thin connecting members connect adjacent sections of the stent, with the members in one plane spaced substantially ninety degrees from those in the other plane as shown in more detail in FIGS. 3 and 4. In other embodiments, the spacing will differ as illustrated in FIG. 6.

The designated detachment zones 3 are designed such that the thin members in at least one of the planes separate under repeated stress placed on the stent 1 after implantation. When both of the members in one of the planes in a particular designated detachment zone 3 separate, the stent is itself separated into independent stent segments 2, as shown in FIG. 2. The thickness or other characteristic of the connecting members in the detachment zones 3 may be selected such that detachment does not occur until some time has passed after implantation, so that the stent segments 2 will already be buried under neointima at the time of detachment and therefore will not move relative to the lumen.

Persons of ordinary skill in the art will appreciate that the basic geometry of the stent segments 2 may take any suitable form, and that the stent segments 2 may be formed of any suitable material. Examples of suitable structures, in addition to those shown herein, for the stent segments 2 include those shown in U.S. Pat. No. 5,733,303 to Israel et al., the disclosure of which is hereby expressly incorporated by reference into this application.

FIG. 3 shows a flat layout of a stent pattern comprising stent segments 2 separated by a designated detachment zone 3. In the illustrated stent, each stent segment 2 can be viewed as being made up of alternating high frequency and low frequency vertical sinusoidal patterns or vertical loop containing sections which are arranged generally in the circumferential direction and which are periodically interconnected. Thus, there is a first loop containing section with loops occurring at a first frequency extending along line 301 and a second loop containing section with loops also occurring at said first frequency extending along line 302. A third loop containing section 303 extending along line 301 and a second loop containing section 303 extending along line 305 has loops occurring at a second frequency that is hight than said first frequency. It is disposed between the first and second loop containing sections and alternately joined to the first and second loop containing sections.

In the illustrated embodiment, the high frequency is in a ratio of 3/2 to the low frequency. Furthermore, in this embodiment, the higher frequency loop containing elements are smaller in width to provide flexibility. The relative widths can be selected so that the high frequency elements are crimpable to the same diameter as the lower frequency elements. However, the stent segments can have other configurations, such as a configuration generally corresponding to a stent configuration disclosed in U.S. Pat. No. 5,733,303.

In the illustrated embodiment three of the low frequency loop containing sections 300 are provided in the detachment zone 3 joining two stent segments 2. Thus, there is an articulation plane 310 between sections 300a and 300b and another articulation plane 312 between the sections 300b and 300c. Two connecting members 315 are disposed in each of the planes 310 and 312, connecting respectively the sections 300a and 300b and 300b and 300c. The members in each plane are spaced from each other an amount that will result in their being 180 degrees apart in the cylindrical stent as will be seen in connection with FIG. 4. The spacing between the members 315 in plane 310 and members 315 in plane 312 is such that, in the cylindrical stent, they will be spaced be substantially 90 degrees.

In this embodiment, each of the connecting members 315 has a cross-sectional area that is sufficiently low to allow fracture of the members and separation under the repeated bending stress placed on the stent after implantation. In general, if it is desired to place a self-articulation point at a given spot in the stent, it must be made narrow in order to locate the expected point of fracture accurately. But, at the same there must be a high probability of fracturing established. Other ways of insuring fracture may be used as disclosed in co-pending Ser. No. 09/204,830 entitled Controlled Detachment Stents and assigned to the same assignee as the present invention, the disclosure of which is hereby incorporated by reference.

Thus, as described above, the stent may be provided at certain points or zones along its length with portions having a cross-sectional area sufficiently low so that the stent segments will detach preferentially under the stress placed on the stent after implantation. Alternatively or additionally, for example, the stent may be provided at the points where fracture is desired along its length with components made of a material that is sufficiently weaker than elsewhere in the stent so that the stent segments will detach preferentially under the stress placed on the stent after implantation as disclosed in Ser. No. 09/204,830. The factors contributing to detachment may be applied individually or in combination. For example, the designated detachment points may have low cross-sectional areas and also may be formed of weaker material.

In the illustrated embodiment, to insure a high probability of fracture, two thin members 315 connect the two adjacent sections so that it is highly likely that repeated bending will fracture the connection. However, if there was only one plane with two members it would be possible that the stent would be deployed such that the two members were in the plane of repeated bend and not perpendicular to it, in which case they would not "work" and would not fracture.

To overcome this problem, in embodiments of the present invention, two planes, each connecting adjacent sections with two thin members are provided. In this arrangement the members can be considered to be in something like a "universal joint" or universal fracture point. Because of the 90-degree separation, if one pair of members is in the bending plane and is not worked or flexed, the other will be in a plane perpendicular to the bending plane and will experience a maximum amount of flexing. With this arrangement, the worst-case is that the plane of at least one fracture connector is at an angle of 45° to the plane of bend. This arrangement insures that the connecting members 315 in at least one of the planes 310 and 312 will fracture to separate the two sections 2.

Figure 4:
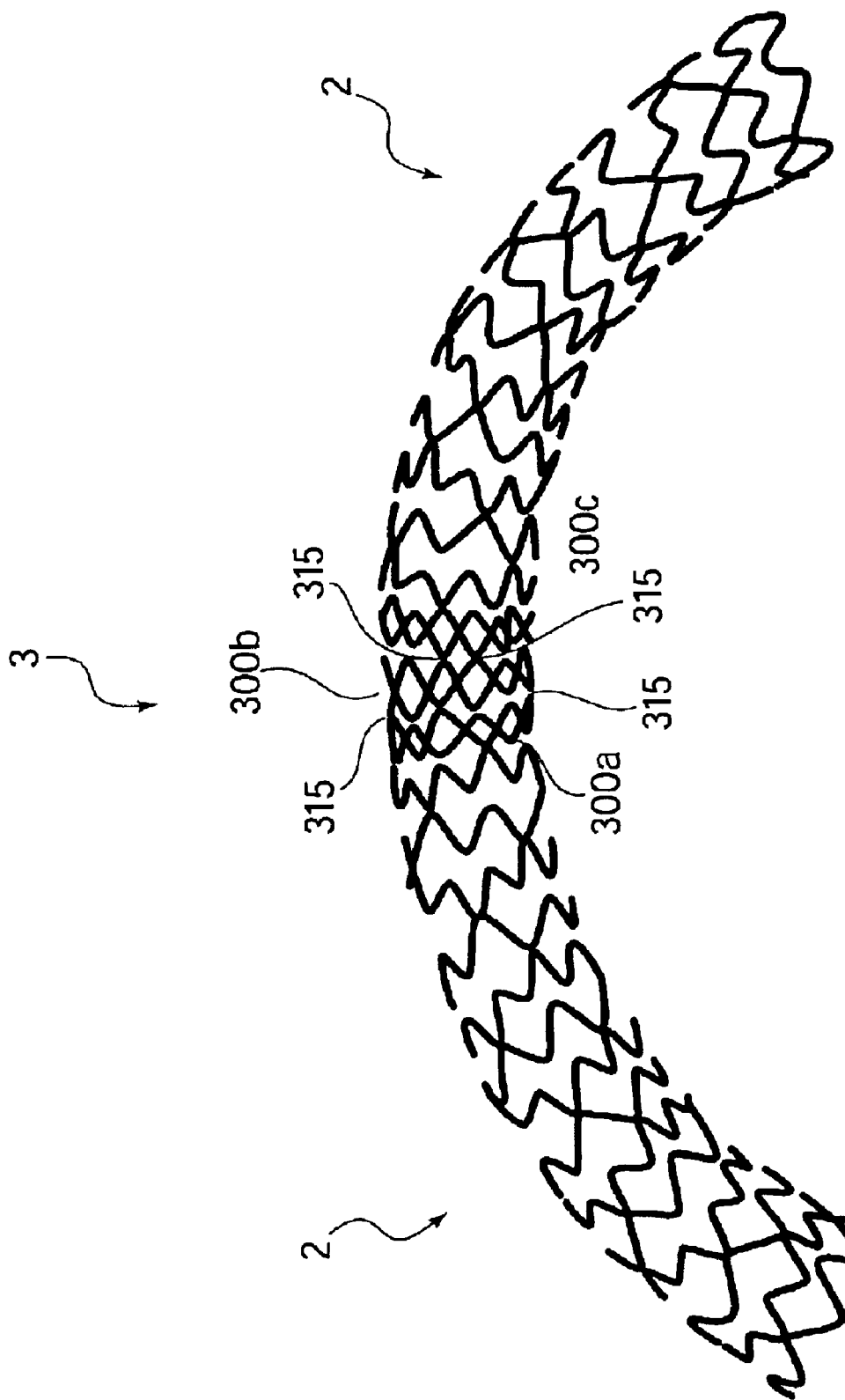
FIG. 4 is a perspective view of the stent of FIG. 3 showing the pairs of thin members spaced approximately ninety degree from each other.

FIG. 4 is a perspective view of the embodiment of FIG. 3 with two stent sections 2 with a detachment zone 3 between them. The stent is shown bent, as often occurs after it is placed in a vessel. If the vessel is an artery, for example, each time the heart beats, the artery tends to straighten out and in doing so places a bending stress on the stent in bending plane, which would coincide with the plane of the paper. Because the stent is long, trauma may be induced at the ends. It is for that reason that it is desired to separate the sections 2, to allow the stent sections 2 to better conform to the curvature of the vessel.

Figure 5:
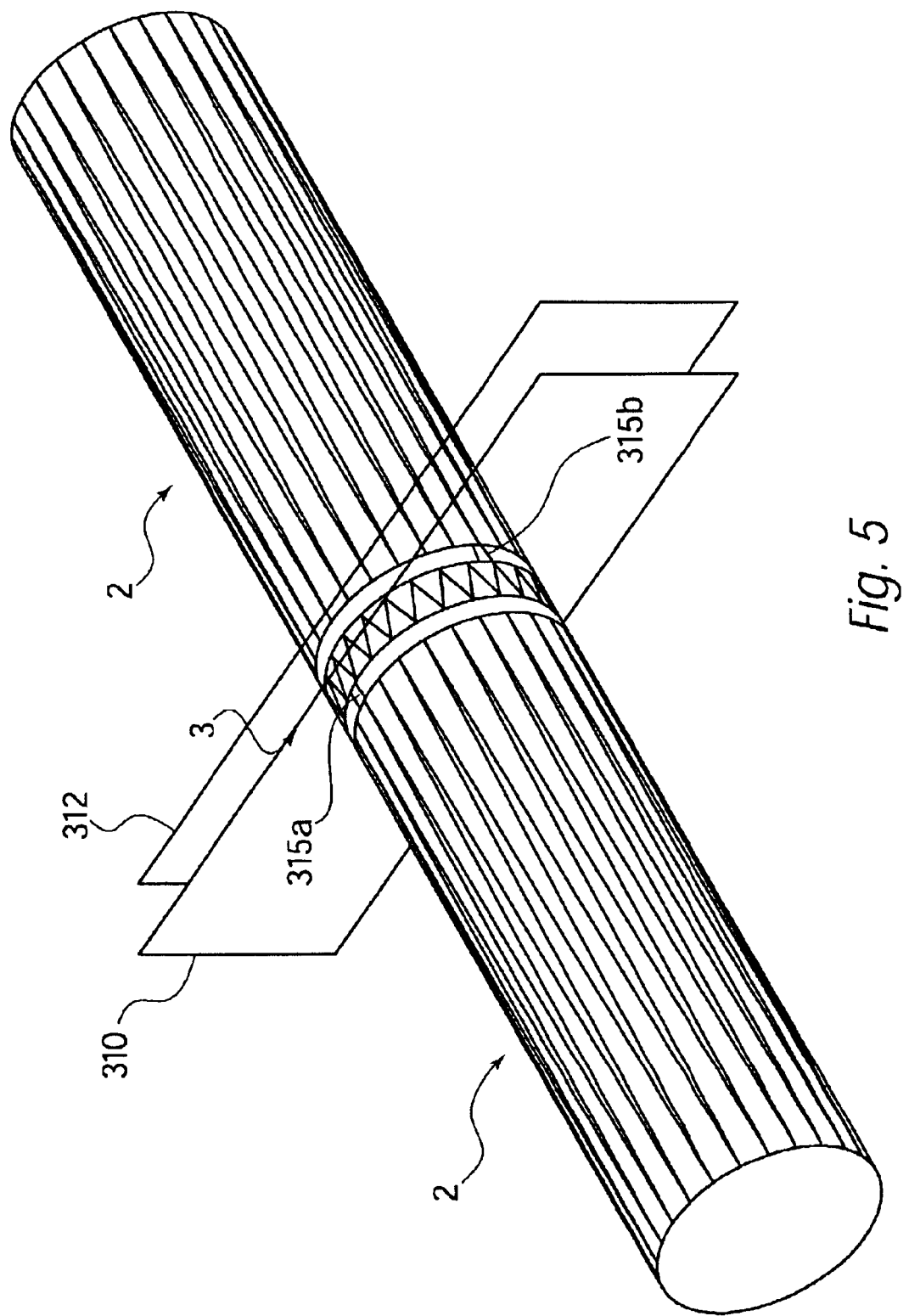
FIG. 5 is a schematic perspective view of the stent of FIG. 3 also showing the pairs of thin members spaced approximately ninety-degrees from each other.

This arrangement of the stent sections 2 and detachment zone 3 between them is also illustrated schematically in FIG. 5. Connecting members 315a are at the top and bottom of the stent and connecting members 315b on the sides, 90 degrees displaced therefrom.

As illustrated in FIG. 4, when bent as shown, the two thin connecting members 315a in the plane 310 between sections 300a and 300b are at the top and bottom of the curved stent and are, thus, in the bending plane and will not be "worked." But, the thin members 315b in plane 312 connecting sections 300b and 300c are on the sides, 90 degrees to the bending plane and will be "worked." In other words, each time the heart beats they will flex. After a certain number of flexures, they will fracture and the two sections 2 will separate.

If the bending place were 90 degrees from what is shown in FIG. 4, the connecting members 315b would be in the bending plane and the connecting members 315a would be worked. Thus, the illustrated arrangement insures that the members 315 in one of thee two planes 310 and 312 will fracture, irrespective of the orientation of the stent, since, as noted above, the worst case is that the members are at a 45 degree angle to the bending plane.

The embodiments illustrated thus far are ones in which there are, for example, six cycles of loops in each of sections 300a, 300b and 300c. This embodiment allows the thin members 315 in each plane 310 and 312 to be spaced 180 degrees as shown in FIG. 6b and the thin members in plane 310 to be spaced 90 degrees from those in the plane 312.

Figure 6C:
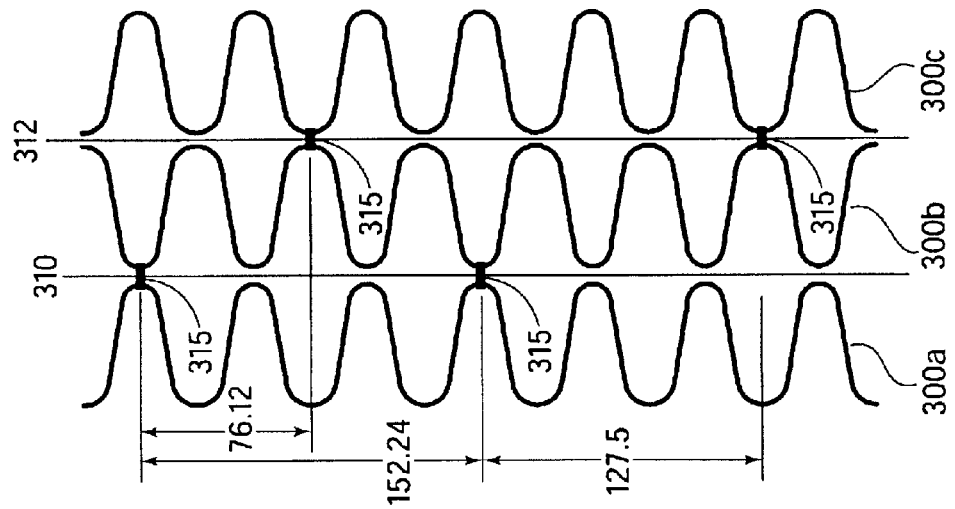
FIGS. 6a–c are flat layouts showing different spacings of the thin members depending on the number loops around the circumference.
Figure 6B:
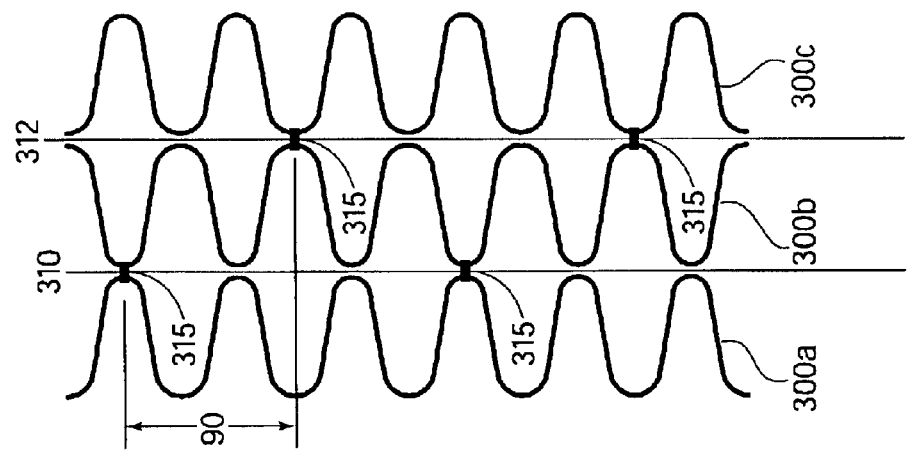
Figure 6A:
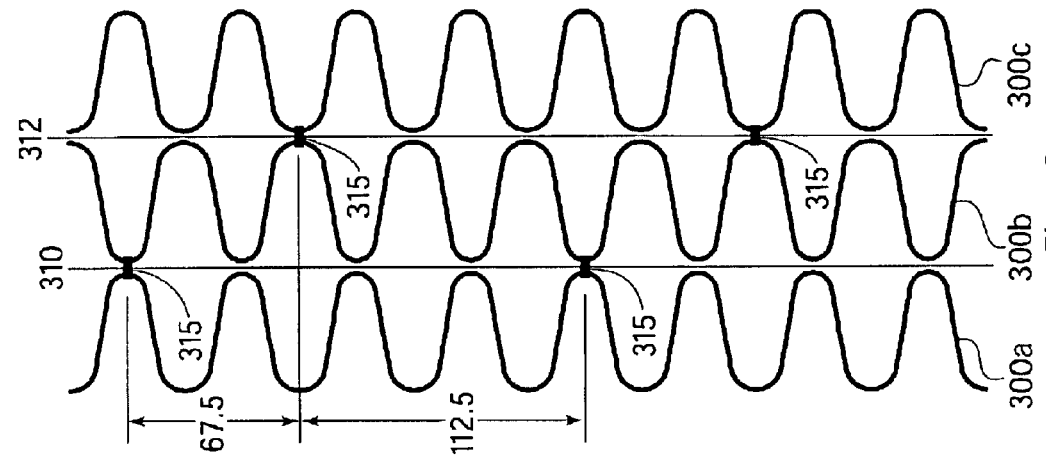

However, there may be embodiments with, for example, eight cycles or seven cycles around the stent as shown in FIGS. 6a and 6c respectively. Thus, in FIG. 6a, the members 315 in plane 310 are spaced either 67.5 or 112.5 degrees from the members 315 in plane 312. Within a plane, the members 315 are spaced 180 degrees from each other because of the even number of cycles. With seven cycles, the even relationship does not hold and within a plane 310 or 312, the spacing is either 152.2 degrees or 207.8 degrees. The spacing between members in planes 310 and 312 is either 76.12 degrees or 127.5 degrees. Other numbers of cycles may be considered. In general, the members in one articulation plane may be spaced from those in the other articulation plane about the circumference of the stent by from about 60 to 140 degrees from each other. Similarly, the two members in each articulation plane may be spaced between about 140 and 220 degrees from each other.

Similar results will be obtained with other numbers of cycles around the cylindrical stent. However, in each case, spacings as close as possible to 180 degrees are established within a plane and as close to 90 degrees as possible between planes. Although not the ideal spacings of FIG. 6b, those of FIG. 6a and FIG. 6e will still result in a pair of members 314 in one of the separation planes 310 or 312 fracturing to separate the two segments 2 of FIGS. 1 and 2.

The embodiments described herein are examples only, as other variations are within the scope of the invention as defined by the appended claims.

What is claimed is:

1. A stent comprising:

a plurality of adjacent stent segments, each made up of a plurality of loop containing sections extending generally in the circumferential direction and which are periodically interconnected, said stent segments spaced from one another;

detachment zones, one between each two adjacent stent segments, each detachment zone comprising a single boo containing section extending generally in the circumferential direction periodically connected on each side to a loop containing section in one of said stent segments such as to form two articulation planes, disposed adjacent to each other, in each of which there are two connecting members, with the members in one articulation plane spaced from those in the other articulation plane about the circumference of the stent by from about 60 to 140 degrees from each other, the connecting members in said articulation planes being easily breakable such that the members in at least one of the planes separate under repeated stress placed on the stent after implantation.

2. A stent according to claim 1 wherein the two members in each articulation plane are spaced between about 140 and 220 degrees from each other.

3. A stent according to claim 1 wherein each stent segment is made up of high frequency and low frequency vertical sinusoidal patterns or vertical loop containing sections which are arranged generally in the circumferential direction and which are periodically interconnected.

4. A stent according to claim 3 comprising a first loop containing section with loops occurring at a first frequency and a second loop containing section with loops also occurring at said first frequency and a third loop containing section having loops occurring at a second frequency that is higher than said first frequency disposed between the first and second loop containing sections and alternately joined to the first and second loop containing sections.

5. A stent according to claim 4 wherein the high frequency is in a ratio of 3/2 to the low frequency.

6. A stent according to claim 4 wherein, the higher frequency loop containing elements are smaller in width to provide flexibility.

7. A stent according to claim 4 wherein, relative widths of high and low frequency loop containing elements are selected so that the high frequency loop containing elements are crimpable to the same diameter as the lower frequency loop containing elements.

8. A stent according to claim 3 wherein first, second and third low frequency loop containing sections are in each detachment zone joining two stent segments with a first articulation plane between the first and second sections and a second articulation plane between the second and third sections.

9. The stent according to claim 8 wherein each of said first, second and third sections contain six cycles of loops and said members in said first plane are spaced 90 degrees from the members in said second plane, with members within a plane are spaced 180 degrees from each other.

10. The stent according to claim 8 wherein each of said first, second and third sections contain eight cycles of loops and said members in said first plane are spaced either 67.5 or 112.5 degrees from the members in said second plane, with members within a plane spaced 180 degrees from each other.

11. The stent according to claim 8 wherein each of said first, second and third sections contain seven cycles of loops and said members in said first plane are spaced either 76.12 or 127.5 degrees from the members in said second plane, with members within a plane spaced either 152.2 degrees or 207.8 degrees from each other.

12. A stent according to claim 1 wherein each of the connecting members has a thin cross section.

13. A stent according to claim 12 wherein each of the connecting members has a cross-sectional area that is sufficiently low to allow fracture of the members and separation under the repeated bending stress placed on the stent after implantation.

14. A stent according to claim 1 wherein each of the connecting members is made of a material that is weaker than elsewhere in the stent.

15. A stent according to claim 1 wherein each of the connecting members has a cross-section that is thin and is made of a material that is weaker than elsewhere in the stent.

* * * * *